(12) United States Patent
Jiang et al.

(10) Patent No.: US 12,721,969 B2
(45) Date of Patent: Sep. 1, 2026

(54) SEPTUM TO FACILITATE BLOOD COLLECTION AND RELATED METHODS

(71) Applicant: Becton, Dickinson and Company, Franklin Lakes, NJ (US)

(72) Inventors: Tao Jiang, Shanghai (CN); Bo Yan, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 571 days.

(21) Appl. No.: 18/033,770

(22) PCT Filed: Oct. 19, 2021

(86) PCT No.: PCT/US2021/055605
§ 371 (c)(1),
(2) Date: Apr. 25, 2023

(87) PCT Pub. No.: WO2022/093581
PCT Pub. Date: May 5, 2022

(65) Prior Publication Data

US 2023/0398326 A1 Dec. 14, 2023

(30) Foreign Application Priority Data

Oct. 29, 2020 (CN) ........................ 202011175867.2

(51) Int. Cl.
*A61M 39/26* (2006.01)
*A61B 5/15* (2006.01)
(Continued)

(52) U.S. Cl.
CPC ... *A61M 25/0075* (2013.01); *A61B 5/150992* (2013.01); *A61M 25/065* (2013.01);
(Continued)

(58) Field of Classification Search
CPC .... A61M 2039/0202; A61M 2039/268; A61M 2039/0081; A61M 2039/1072;
(Continued)

(56) References Cited

U.S. PATENT DOCUMENTS 4,324,239 A 4/1982 Gordon et al.
5,845,943 A * 12/1998 Ramacier, Jr. .......... F16L 37/42 285/317
(Continued)

FOREIGN PATENT DOCUMENTS

CN 214388487 U 10/2021
FR 2995654 A1 * 3/2014 ............ F16L 37/407
(Continued)

*Primary Examiner* — Emily L Schmidt
*Assistant Examiner* — Martin A Radomski
(74) *Attorney, Agent, or Firm* — Kirton McConkie; Whitney Blair; Kevin Stinger

(57) ABSTRACT

A septum may include a housing and a hollow body that slides with respect to the housing from a closed position to an open position. The hollow body may include one or more holes. The septum may include a first seal coupled to the distal end and a second seal coupled to the proximal end. In response to the hollow body being in the closed position, the second seal may block a proximal opening of the housing, and the holes may be disposed within the housing. In response to the hollow body sliding from the closed position to the open position, the holes may be disposed distal to the housing, and the second seal may be removed from the proximal opening of the housing such that fluid may flow proximally into the plurality of holes and through the proximal opening of the housing.

18 Claims, 3 Drawing Sheets

(51) Int. Cl.

| | |
|---|---|
| ***A61M 25/00*** | (2006.01) |
| ***A61M 25/06*** | (2006.01) |
| ***A61M 39/24*** | (2006.01) |
| *A61M 39/00* | (2006.01) |
| *A61M 39/02* | (2006.01) |
| *A61M 39/10* | (2006.01) |
| *F16L 37/42* | (2006.01) |

(52) U.S. Cl.

CPC ..... *A61M 39/24* (2013.01); *A61M 2039/0081* (2013.01); *A61M 2039/0202* (2013.01); *A61M 2039/1072* (2013.01); *A61M 2039/2433* (2013.01); *A61M 2039/267* (2013.01); *A61M 2039/268* (2013.01); *F16L 37/42* (2013.01)

(58) Field of Classification Search

CPC ......... A61M 2039/267; A61M 25/0612; F16L 37/42; F16K 1/303; A61J 1/2048

See application file for complete search history.

(56) References Cited

U.S. PATENT DOCUMENTS

| | | | | |
|---|---|---|---|---|
| 6,113,068 | A * | 9/2000 | Ryan | A61M 39/045 604/905 |
| 7,926,783 | B1 * | 4/2011 | Liu | F16L 37/23 251/149.6 |
| 9,101,746 | B2 | 8/2015 | Stout et al. | |
| 9,750,920 | B2 | 9/2017 | Vincent et al. | |
| 2003/0050610 | A1 | 3/2003 | Newton et al. | |
| 2003/0093061 | A1 | 5/2003 | Ganem | |
| 2004/0011983 | A1 * | 1/2004 | Maiville | F16L 37/42 604/905 |
| 2010/0004618 | A1 * | 1/2010 | Rondeau | A61M 39/26 604/407 |
| 2010/0108681 | A1 * | 5/2010 | Jepson | A61M 39/1011 220/278 |
| 2010/0249725 | A1 * | 9/2010 | Cote, Sr. | A61M 39/26 604/249 |
| 2011/0015580 | A1 * | 1/2011 | Stroup | A61M 39/12 604/207 |
| 2013/0310764 | A1 | 11/2013 | Burkholz et al. | |
| 2015/0126958 | A1 * | 5/2015 | Sanders | A61J 1/2065 285/330 |
| 2015/0151088 | A1 | 6/2015 | Lim et al. | |
| 2016/0144109 | A1 * | 5/2016 | Stroup | A61M 5/16881 604/248 |
| 2017/0307123 | A1 * | 10/2017 | Liu | F16L 37/23 |
| 2019/0086013 | A1 * | 3/2019 | Hafele | F16L 37/23 |

FOREIGN PATENT DOCUMENTS

| | | | |
|---|---|---|---|
| JP | 2017503598 | A | 2/2017 |
| JP | 2018531760 | A | 11/2018 |
| WO | 2006078305 | A1 | 7/2006 |

* cited by examiner

SEPTUM TO FACILITATE BLOOD COLLECTION AND RELATED METHODS

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to septa and related devices and methods. In some embodiments, a septum may include a housing, which may include a distal opening, a proximal opening, and a lumen extending from the distal opening to the proximal opening. In some embodiments, the housing may be generally cylindrical.

In some embodiments, the septum may include a hollow body, which may slide with respect to the housing from a closed position to an open position. In some embodiments, the hollow body may be generally cylindrical. In some embodiments, the hollow body may be at least partially disposed within the housing. In some embodiments, the hollow body may include a distal end, a proximal end, and a passageway extending between the distal end and the proximal end. In some embodiments, the hollow body may include one or more holes.

In some embodiments, the septum may include a first seal, which may be coupled to the distal end of the hollow body. In some embodiments, the septum may include a second seal, which may be coupled to the proximal end of the hollow body. In some embodiments, in response to the hollow body being in the closed position, the second seal may block the proximal opening of the housing, and the holes may be disposed within the housing. In some embodiments, in response to the hollow body sliding from the closed position to the open position, the holes may be disposed distal to the housing, and the second seal may be removed from the proximal opening of the housing such that fluid may flow proximally into the holes and through the proximal opening of the housing.

In some embodiments, the first seal may extend proximal to the holes and may cover the holes. In some embodiments, the first seal may include a one-way check valve. In some embodiments, the first seal and/or the second seal may be constructed of silicon or another suitable material. In some embodiments, the second seal may include a plug, a duck valve, or another suitable seal.

In some embodiments, the proximal end of the hollow body may include a first cam element. In some embodiments, the first cam element may include a first groove. In some embodiments, an inner surface of the housing may include a rail. In some embodiments, the septum may include a second cam element, which may be disposed within the housing. In some embodiments, the second cam element may include a second groove and a stop surface. In some embodiments, the septum may include a spring, which may be disposed within the housing. In some embodiments, the spring may bias the second cam element proximally against the first cam element.

In some embodiments, when the hollow body is in the closed position, the rail may be disposed within the first groove and the second groove. In some embodiments, when the hollow body is in the closed position, the rail may prevent rotation of the second cam element with respect to the first cam element. In some embodiments, in response to distal movement of the first cam and the second cam such that the rail is removed from second groove, the second cam element may rotate such that the rail is not aligned with the second groove. In some embodiments in response to distal movement of the first cam and the second cam such that the rail is removed from second groove, the stop surface of the second cam may contact the rail to prevent proximal movement of the second cam and lock the hollow body in the open position. In some embodiments, in response to movement of the hollow body distally beyond the open position, the hollow body may be unlocked and configured to return to the closed position.

In some embodiments, a catheter assembly may include a catheter adapter, which may include a lumen extending through the catheter adapter. In some embodiments, the housing may be secured within the lumen of the catheter adapter. In some embodiments, a catheter may extend distally from the catheter adapter. In some embodiments, in response to the hollow body sliding from the closed position to the open position, the holes may be disposed distal to the housing, and the second seal may be removed from the proximal opening of the housing such that fluid from the lumen of the catheter adapter may flow proximally into the holes and through the proximal opening of the housing.

In some embodiments, the septum may include an O-ring, which may be coupled to a distal end of the housing. In some embodiments, the O-ring may be disposed between the housing and the catheter adapter and may prevent fluid from flowing between an outer surface of the housing and an inner surface of the catheter adapter.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
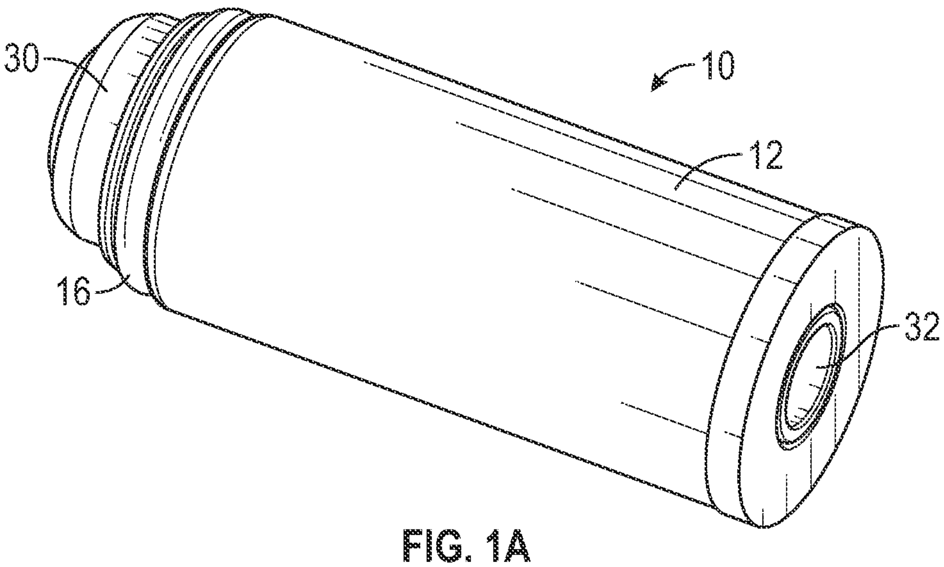
FIG. 1A is an upper perspective view of an example septum, illustrating an example proximal end of the septum, according to some embodiments.
Figure 1B:
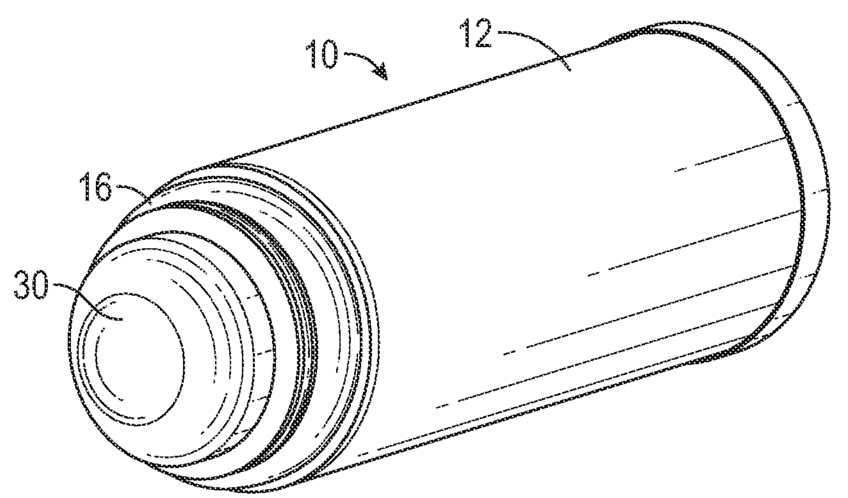
FIG. 1B is an upper perspective view of the septum of FIG. 1A, illustrating an example distal end of the septum, according to some embodiments.
Figure 2A:
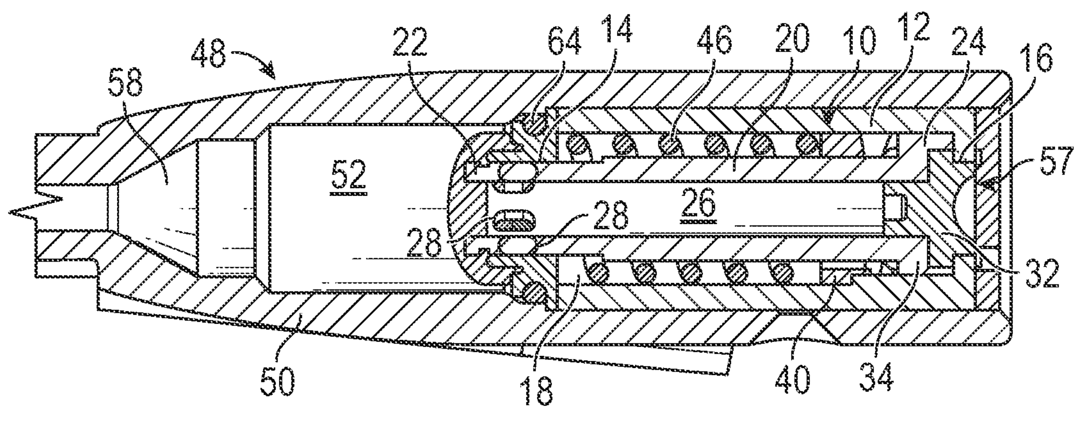
FIG. 2A is a cross-sectional view of an example catheter assembly, illustrating the septum of FIG. 1A in a closed configuration, according to some embodiments.
Figure 2B:
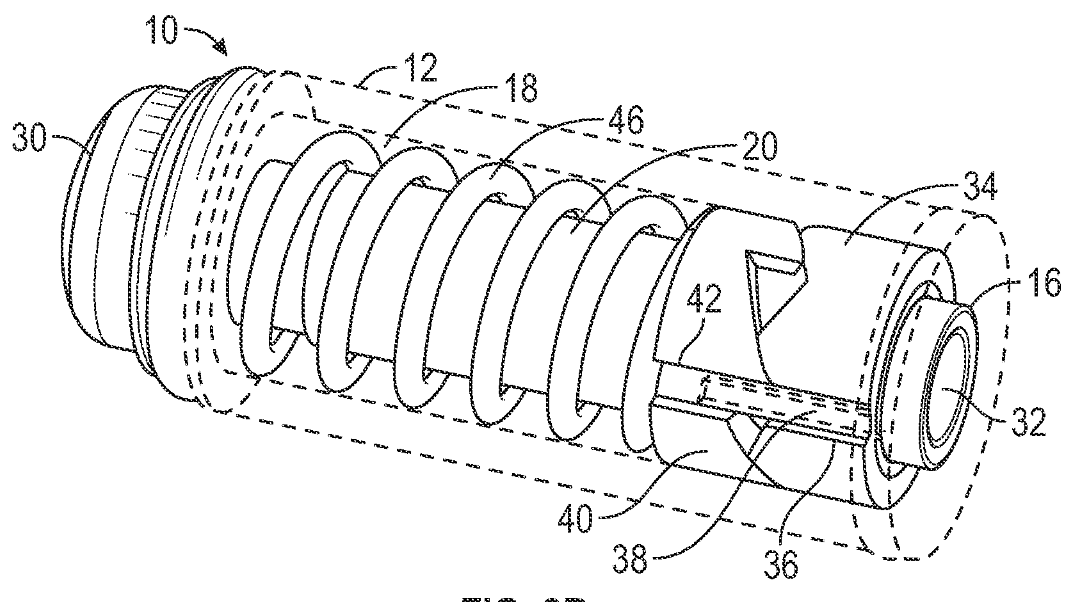
FIG. 2B is an upper perspective view of the septum of FIG. 1A in the closed configuration, according to some embodiments.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

Referring now to FIGS. 1A-4, in some embodiments, a septum 10 may include a housing 12, which may include a distal opening 14, a proximal opening 16, and a lumen 18 extending from the distal opening 14 to the proximal opening 16. In some embodiments, the housing 12 may be generally cylindrical.

Figure 3A:
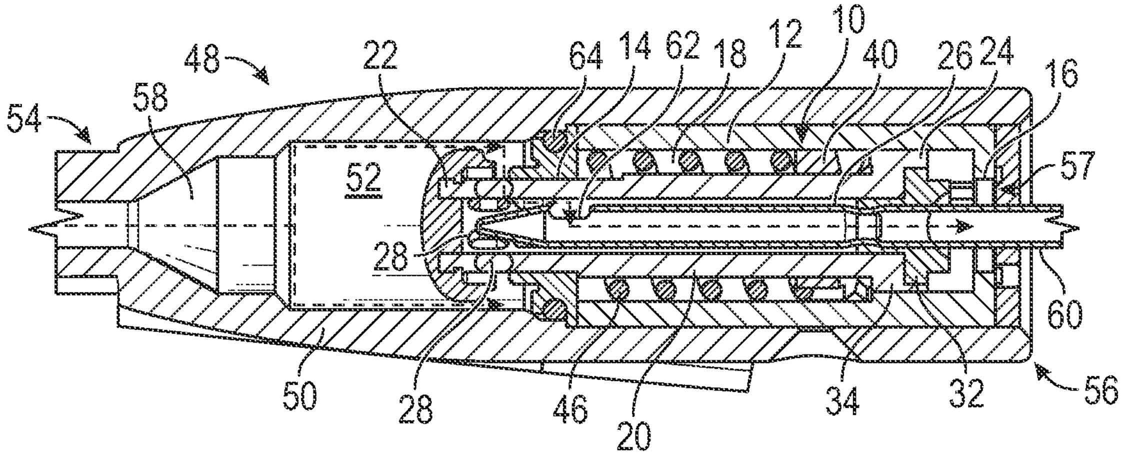
FIG. 3A is a cross-sectional view of the catheter assembly of FIG. 2A, illustrating the septum in an open configuration, according to some embodiments.
Figure 3B:
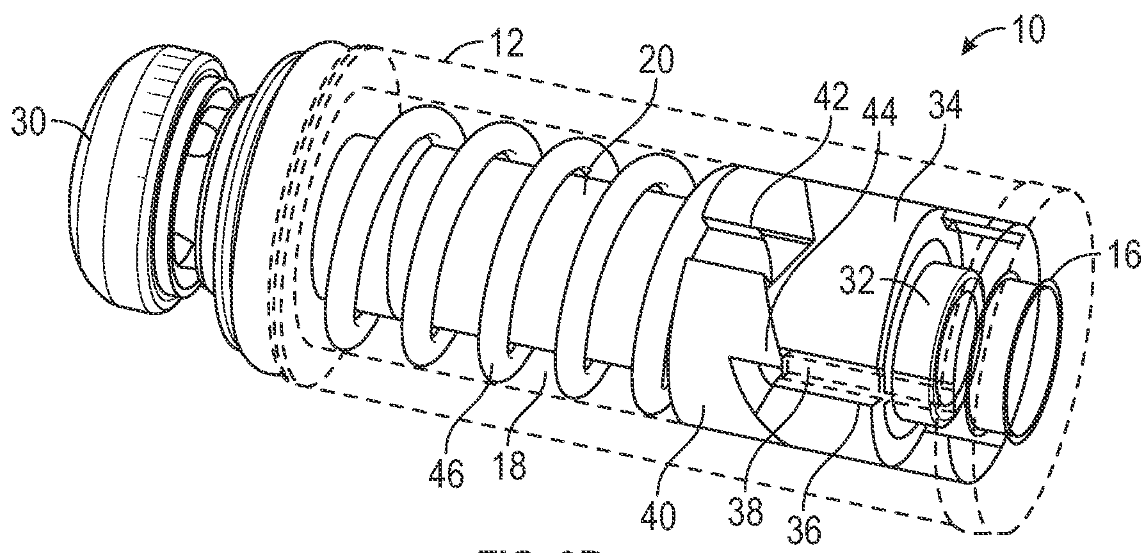
FIG. 3B is an upper perspective view of the septum of FIG. 1A in the closed configuration, according to some embodiments.

In some embodiments, the septum 10 may include a hollow body 20, which may slide with respect to the housing 12 from a closed position, illustrated, for example, in FIGS. 1A-2B, to an open position, illustrated, for example, in FIGS. 3A-3B. In some embodiments, the hollow body 20 may be generally cylindrical. For example, an outer surface of the hollow body 20 may be generally cylindrical and/or an inner surface of the hollow body 20 may be generally cylindrical. In some embodiments, the hollow body 20 may be at least partially disposed within the housing 12. In some embodiments, the hollow body 20 may include a distal end 22, a proximal end 24, and a passageway 26 extending between the distal end 22 and the proximal end 24. In some embodiments, the hollow body 20 may include one or more holes 28, which may be disposed at the distal end 22 of the hollow body 20.

In some embodiments, the septum 10 may include a first seal 30, which may be coupled to the distal end 22 of the hollow body 20. In some embodiments, the first seal 30 may seal a distal opening of the distal end 22 of the hollow body 20, preventing fluid from flowing through the distal opening of the distal end 22. In some embodiments, the first seal 30 may include a rounded cap. In some embodiments, the septum 10 may include a second seal 32, which may be coupled to the proximal end 24 of the hollow body 20. In some embodiments, the second seal 32 may seal a proximal opening of the proximal end 24 of the hollow body 20, preventing fluid from flowing through the proximal opening of the proximal end 24. In some embodiments, the first seal 30 and/or the second seal 32 may be constructed of silicon or another suitable material.

In some embodiments, in response to the hollow body 20 being in the closed position, the second seal 32 may block the proximal opening 16 of the housing 12, and the holes 28 may be disposed within the housing 12. In some embodiments, the hollow body 20 may slide from the closed position to the open position in response to application of a first external force at proximal end of the septum 10. In some embodiments, in response to the hollow body 20 sliding from the closed position to the open position, the holes 28 may be disposed distal to the housing 12, and the second seal 32 may be removed from the proximal opening 16 of the housing 12 such that fluid may flow proximally into the holes 28 and through the proximal opening 16 of the housing 12.

In some embodiments, the proximal end 24 of the hollow body 20 may include a first cam element 34, which may not rotate. In some embodiments, the first cam element 34 may include a first slot or groove 36. In some embodiments, an inner surface of the housing 12 may include a rail 38. In some embodiments, the septum 10 may include a second cam element 40, which may be disposed within the housing 12 and which may be configured to rotate. In some embodiments, the second cam element 40 may include a second slot or groove 42 and a stop surface 44.

In some embodiments, the septum 10 may include a spring 46, which may be disposed within the housing 12 and around the hollow body 20. In some embodiments, a proximal end of the spring 46 may contact the second cam element 40. In some embodiments, the spring 46 may bias the second cam element 40 proximally against the first cam element 34. Thus, in some embodiments, the spring 46 may bias the hollow body 20 in the closed position. In some embodiments, the spring 46 may include a coil. In some embodiments, the spring 46 may be constructed of metal, an elastomer, or another suitable material.

In some embodiments, when the hollow body 20 is in the closed position, the rail 38 may be disposed within the first groove 36 and the second groove 42. In some embodiments, when the hollow body 20 is in the closed position, the rail 38 may prevent rotation of the second cam element 40 with respect to the first cam element 34. In some embodiments, in response to distal movement of the first cam element 34 and the second cam element 40 such that the rail 38 is removed from second groove 42, the second cam element 40 may rotate such that the rail 38 is not aligned with the second groove 42.

In some embodiments in response to distal movement of the first cam element 34 and the second cam element 40 such that the rail 38 is removed from second groove 42, the stop surface 44 of the second cam element 40 may contact the rail 38 to prevent proximal movement of the second cam element 40 and lock the hollow body 20 in the open position, even after the first external force is removed. In some embodiments, the first cam element 34 and the second cam element 40 may include one or more angled surfaces or teeth, which may be in contact. In some embodiments, the contact between the angled surfaces of the teeth of the first cam element 34 and the second cam element 40, in conjunction with force applied by the spring 46 in a proximal direction, may result in rotation of the second cam element 40 with respect to the first cam element 34. In some embodiments, the stop surface 44 may stop rotation of the second cam element 40.

Figure 4:
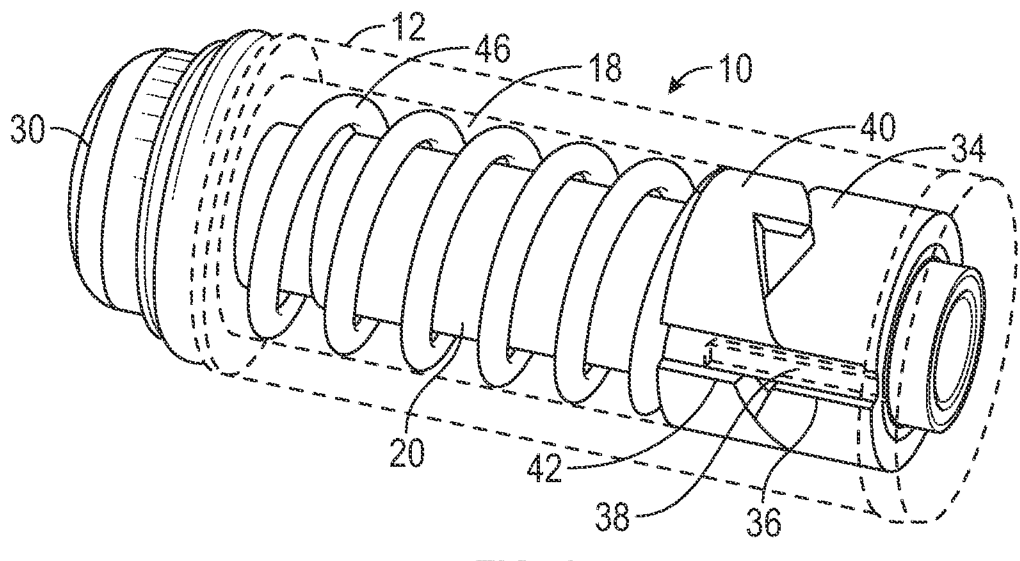
FIG. 4 is an upper perspective view of the septum of FIG. 1A returned to the closed configuration, according to some embodiments.

In some embodiments, in response to movement of the hollow body 20 distally beyond the open position, the hollow body 20 may be unlocked and configured to return to the closed position, as illustrated, for example, in FIG. 4. In some embodiments, the hollow body 20 may be moved distally beyond the open position by application of a second external force to the proximal end of the septum 10. In some embodiments, the hollow body 20 may be unlocked when the rail 38 is aligned with the second groove 42 or another groove of the second cam element 40. In some embodiments, the other groove of the second cam element 40 may be similar to the second groove 42 and may be spaced apart from the second groove 42 around a circumference of the second cam element 40. In some embodiments, the hollow body 20 may slide to a position distal to the open position before locking in the open position.

In some embodiments, a catheter assembly 48 may include a catheter adapter 50, which may include a lumen 52 extending through the catheter adapter 50. In some embodiments, the catheter adapter 50 may include a distal end 54, a proximal end 56, and the lumen 52 extending through the distal end 54 and the proximal end 56. In some embodiments, the proximal end 56 may include a proximal opening 57. In some embodiments, the housing 12 may be secured within the lumen 52 of the catheter adapter 50. In some embodiments, a catheter 58 may extend distally from the catheter adapter 50. In some embodiments, in response to the hollow body 20 sliding from the closed position to the open position, the holes 28 may be disposed distal to the housing 12, and the second seal 32 may be removed from the proximal opening 16 of the housing 12 such that fluid from the lumen 52 of the catheter adapter 50 may flow proximally into the holes 28 and through the proximal opening 16 of the housing 12. In some embodiments, in response to the hollow body 20 being in the closed position, the second seal 32 may block the proximal opening 16 of the housing 12, and the holes 28 may be disposed within the housing 12. Thus, the passageway 26 may not be in fluid communication with the lumen 52 of the catheter adapter 50.

In some embodiments, a needle assembly, which may include an introducer needle, may be coupled to the proximal end 56 of the catheter adapter 50. In some embodiments, after the needle assembly is uncoupled and removed from the catheter assembly 48, the blood collection device may be coupled to and/or inserted within the proximal end 56 of the catheter adapter 50. In some embodiments, the blood collection device may include a needle 60. In some embodiments, the needle 60 may include a sharp distal tip. In other embodiments, the needle 60 may be blunt. In some embodiments, the second seal 32 may be pierced by the needle 60. In some embodiments, the needle 60 may extend through the second seal 32. In some embodiments, prior to moving the hollow body 20 to the closed position, a user may suction out blood from inside of the hollow body 20 and/or prime the catheter assembly 48.

In some embodiments, an opening 62 of the needle 60 of the blood collection device may be disposed within the hollow body 20 proximal to or proximate the holes 28. In some embodiments, when the hollow body 20 is in the open position, blood may be configured to flow from the patient proximally within the catheter assembly 48 from the lumen 52 of the catheter adapter 50, through the holes 28, and into the opening of the needle 60. In some embodiments, the needle 60 may include the introducer needle.

In some embodiments, the septum 10 may include an O-ring 64, which may be coupled to the distal end of the housing 12. For example, the housing 12 may include an annular groove, which may include the O-ring 64. In some embodiments, the O-ring 64 may be disposed between the housing 12 and the catheter adapter 50 and may prevent fluid from flowing between an outer surface of the housing 12 and an inner surface of the catheter adapter 50. In some embodiments, the housing 12 may be integrally formed or monolithically formed as a single unit.

Figure 5A:
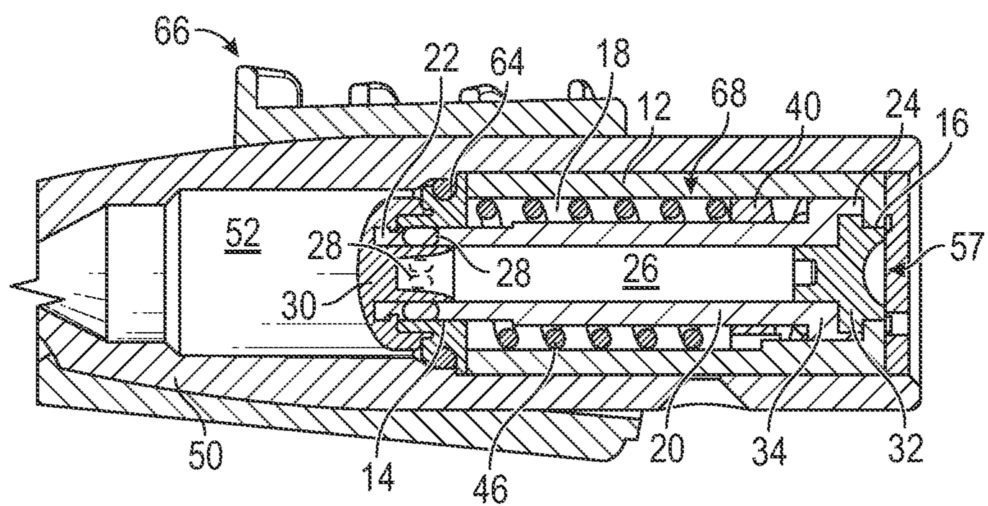
FIG. 5A is a cross-sectional view of another example catheter assembly, illustrating another example septum in a closed configuration, according to some embodiments.
Figure 5B:
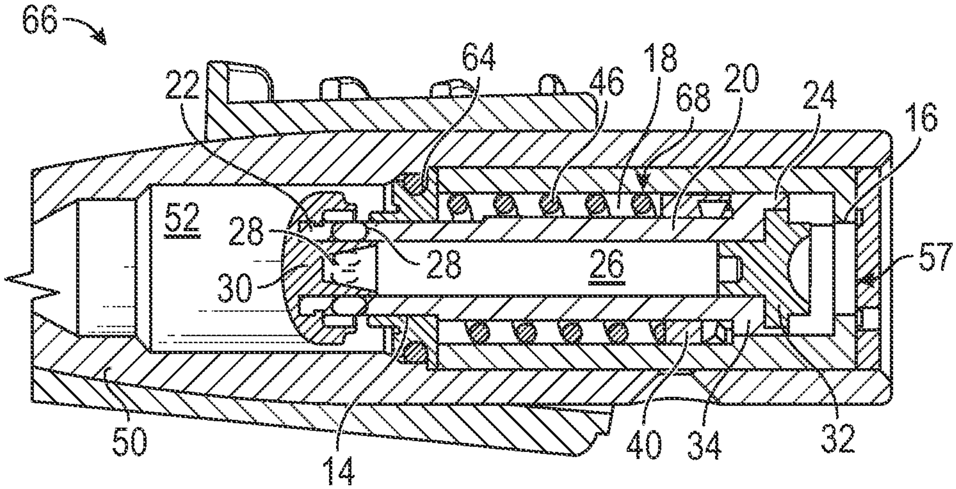
FIG. 5B is an upper perspective view of the catheter assembly of FIG. 5A, illustrating the septum in an open configuration, according to some embodiments.

Referring now to FIGS. 5A-5B, a catheter assembly 66 is illustrated, according to some embodiments. In some embodiments, the catheter assembly 66 may include a septum 68. In some embodiments, the catheter assembly 66 and the septum 68 may similar or identical to the catheter assembly 48 and the septum 10 described with respect to FIGS. 1A-4 in terms of one or more included components and/or operation. In some embodiments, the first seal 30 may extend proximal to the holes 28 and may cover the holes 28. In some embodiments, the first seal 30 may include a one-way check valve. In some embodiments, the second seal 32 may include a plug, a duck valve, or another suitable seal.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A catheter assembly, comprising:

a catheter adapter, comprising a lumen extending through the catheter adapter;

a catheter extending distally from the catheter adapter; and a septum, comprising:

a housing secured within the lumen of the catheter adapter, the housing comprising a distal opening, a proximal opening, and a lumen extending from the distal opening to the proximal opening;

a hollow body that slides with respect to the housing from a closed position to an open position, wherein the hollow body is at least partially disposed within the housing, wherein the hollow body comprises a distal end, a proximal end, and a passageway extending between the distal end and the proximal end, wherein the hollow body comprises a plurality of holes;

a first seal coupled to the distal end of the hollow body; and a second seal coupled to the proximal end of the hollow body, wherein in response to the hollow body being in the closed position, the second seal blocks the proximal opening of the housing and the plurality of holes are disposed within the housing, wherein in response to the hollow body sliding from the closed position to the open position, the plurality of holes are disposed distal to the housing and the second seal is removed from the proximal opening of the housing such that fluid from the lumen of the catheter adapter may flow proximally into the plurality of holes and through the proximal opening of the housing, wherein the proximal end of the hollow body comprises a first cam element, wherein the first cam element comprises a first groove, wherein an inner surface of the housing comprises a rail, wherein the septum further comprises:

a second cam element disposed within the housing and comprising a second groove and a stop surface;

a spring disposed within the housing and biasing the second cam element proximally against the first cam element, wherein when the hollow body is in the closed position, the rail is disposed within the first groove and the second groove and prevents rotation of the second cam element with respect to the first cam element, wherein in response to distal movement of the first cam element and the second cam element such that the rail is removed from second groove, the second cam element rotates such that the rail is not aligned with the second groove, and the stop surface of the second cam element contacts the rail to prevent proximal movement of the second cam element and lock the hollow body in the open position.

2. The catheter assembly of claim 1, wherein in response to movement of the hollow body distally beyond the open position, the hollow body is unlocked and is configured to return to the closed position.

3. The catheter assembly of claim 1, wherein the first seal extends proximal to the plurality of holes and covers the plurality of holes, wherein the first seal comprises a one-way check valve.

4. The catheter assembly of claim 1, wherein the spring comprises a coil that surrounds the hollow body.

5. The catheter assembly of claim 1, wherein the housing is generally cylindrical.

6. The catheter assembly of claim 1, wherein the hollow body is generally cylindrical.

7. The catheter assembly of claim 1, wherein the first seal comprises a rounded cap.

8. The catheter assembly of claim 1, further comprising an O-ring coupled to a distal end of the housing and disposed between the housing and the catheter adapter.

9. The catheter assembly of claim 1, wherein the second seal comprises a plug or a duck valve.

10. A septum, comprising:

a housing, comprising a distal opening, a proximal opening, and a lumen extending from the distal opening to the proximal opening;

a hollow body that slides with respect to the housing from a closed position to an open position, wherein the hollow body is at least partially disposed within the housing, wherein the hollow body comprises a distal end, a proximal end, and a passageway extending between the distal end and the proximal end, wherein the hollow body comprises a plurality of holes;

a first seal coupled to the distal end of the hollow body; and a second seal coupled to the proximal end of the hollow body, wherein in response to the hollow body being in the closed position, the second seal blocks the proximal opening of the housing and the plurality of holes are disposed within the housing, wherein in response to the hollow body sliding from the closed position to the open position, the plurality of holes are disposed distal to the housing and the second seal is removed from the proximal opening of the housing such that fluid may flow proximally into the plurality of holes and through the proximal opening of the housing, wherein the proximal end of the hollow body comprises a first cam element, wherein the first cam element comprises a first groove, wherein an inner surface of the housing comprises a rail, wherein the septum further comprises:

a second cam element disposed within the housing and comprising a second groove and a stop surface;

a spring disposed within the housing and biasing the second cam element proximally against the first cam element, wherein when the hollow body is in the closed position, the rail is disposed within the first groove and the second groove and prevents rotation of the second cam element with respect to the first cam element, wherein in response to distal movement of the first cam element and the second cam element such that the rail is removed from second groove, the second cam element rotates such that the rail is not aligned with the second groove, and the stop surface of the second cam element contacts the rail to prevent proximal movement of the second cam element and lock the hollow body in the open position.

11. The septum of claim 10, wherein in response to movement of the hollow body distally beyond the open position, the hollow body is unlocked and is configured to return to the closed position.

12. The septum of claim 10, wherein the spring comprises a coil that surrounds the hollow body.

13. The septum of claim 10, wherein the first seal comprises a rounded cap.

14. The septum of claim 10, wherein the first seal extends proximal to the plurality of holes and covers the plurality of holes, wherein the first seal comprises a one-way check valve.

15. The septum of claim 10, wherein the housing is generally cylindrical.

16. The septum of claim 10, wherein the hollow body is generally cylindrical.

17. The septum of claim 10, further comprising an O-ring coupled to a distal end of the housing.

18. The septum of claim 10, wherein the second seal comprises a plug or a duck valve.

* * * * *